United States Patent [19]

Sanderson et al.

[11] 4,196,166

[45] * Apr. 1, 1980

[54] STERILIZED STORAGE CONTAINER

[75] Inventors: Roger S. Sanderson, 24662 Santa Clara, Dana Point, Calif. 92629; Robert C. Whelchel, Newport Beach, Calif.

[73] Assignee: Roger S. Sanderson, Dana Point, Calif.

[*] Notice: The portion of the term of this patent subsequent to Apr. 17, 1996, has been disclaimed.

[21] Appl. No.: 703,044

[22] Filed: Jul. 6, 1976

Related U.S. Application Data

[63] Continuation-in-part of Ser. No. 640,824, Dec. 15, 1975, abandoned.

[51] Int. Cl.² ............... A61L 3/00; A61L 5/00; A61L 7/00
[52] U.S. Cl. .................... 422/33; 422/114; 422/26; 422/300; 220/201; 137/468
[58] Field of Search ............... 220/201, 202; 137/72, 137/457, 468; 21/91, 92, 93, 94, 95, 96, 97, 98, 99, 100, 56, 60, 83, 84; 236/99 F, 99 K, 99 G; 215/270, 311, 260

[56] References Cited

U.S. PATENT DOCUMENTS

| 2,008,835 | 7/1935 | Rawcliffe | 137/468 |
|---|---|---|---|
| 2,455,305 | 11/1948 | Heva | 137/468 |
| 2,591,767 | 4/1952 | Andres | 220/203 |
| 2,698,022 | 12/1954 | Fahnoe | 137/468 |
| 2,829,796 | 4/1958 | Dieny | 220/203 |
| 3,561,918 | 2/1971 | Ray | 206/363 |
| 3,621,951 | 11/1971 | Schmid | 137/468 |
| 3,762,595 | 10/1973 | Green et al. | 220/202 |
| 4,038,034 | 7/1977 | Nakajima | 137/468 |

FOREIGN PATENT DOCUMENTS 1642161 8/1970 Fed. Rep. of Germany .

Primary Examiner—Joseph Man-Fu Moy
Attorney, Agent, or Firm—Knobbe, Martens, Olson, Hubbard & Bear

[57] ABSTRACT

A sealed container provided with a valve opening and a resilient valve member self-biased into closing position. The valve is manually openable by a lever which is held in the open position by a rigid fuse-like element which melts after being subjected to sterilizing temperatures long enough to sterilize the container and its contents. The valve then closes sealing the container. The valve and a gasket between the container lid and base will permit leakage out of the box to permit the withdrawal of steam from the container when a vacuum is applied to the container exterior but will prevent reverse flow so that a vacuum is maintained within the container once one is created. The vacuum may be released by opening the valve, which simultaneously cocks it for the next sterilizing operation.

An alternate approach includes a disposable, resilient valve member which plugs into a hole in the wall of the container and covers a valve orifice into the container. A washer-like fuse element fits into the valve member to bias it into an open position. When the fuse melts after sterilization, the valve member will snap into closed position.

24 Claims, 10 Drawing Figures

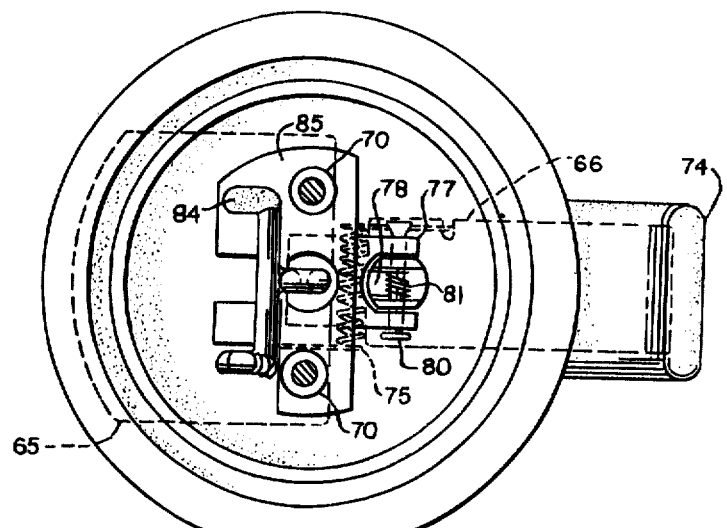

STERILIZED STORAGE CONTAINER

CROSS REFERENCE TO RELATED APPLICATION

This invention is a continuation-in-part of U.S. patent application Ser. No. 640,824 filed Dec. 15, 1975 entitled STERILIZED STORAGE CONTAINER, now abandoned.

This invention relates to an improved apparatus for storing sterile items while they are being sterilized, while they are being stored awaiting use, while they are in the process of being used, and after they have been used and are awaiting resterilization.

The most commonly used method for sterilizing surgical instruments and other medical items is to place them in towels which are enclosed in a sheet and taped shut for placement in a sterilizing autoclave. Sterilizing steam applied to the interior of the autoclave penetrates the porus material surrounding the items to be sterilized. The moisture is removed by a drying cycle within the autoclave. The sterile package is then either used immediately or placed in storage for future use. If the pack has not been used in a period of time, typically twenty days, it must be returned to the autoclave for resterilization. It is estimated that two-thirds of sterilization work load in many hospitals is for items that were not used within the shelf life of the pack. This of course is an expensive and inefficient procedure.

Another shortcoming of the towel arrangement is that, unless adequate labeling is used, the contents within the towel are unknown. Once the package is opened to check the contents, the sterilization is, of course, lost unless the contents are immediately used. If the contents are not what the user desires, then the sterilization of that particular package must be repeated.

Thus, a need exists for a practical and reliable system for handling sterile items and for maintaining sterility. A container surrounding the items to be sterilized could be completely sealed before being placed in the autoclave, but the contents are then not subjected to a sterilizing steam. Instead, the atmosphere within the sealed container would be closer to dry heat sterilization which requires higher temperatures and longer periods of time than does moist heat. Also, an autoclave typically has significant pressure variations as a result of vacuum phases exhausting air and steam, and a pressure phase applying steam. Thus, a sealed container would have these pressure variations applied to its exterior which might cause breakage or damage to the container.

In the above-referenced patent application, a system is disclosed wherein a container is placed within an autoclave with its lid slightly open, and means are provided for automatically closing the lid at a predetermined time near the end of the sterilizing cycle. While this system is highly desirable, moving the entire lid at the desired time does introduce certain complexities.

SUMMARY OF THE INVENTION

The present invention includes a closed container for holding the items to be sterilized and stored, and a novel valve means which is open during sterilization and then automatically closes at a desired point. The valve is held open by temperature responsive fuse means which is rigid at normal room terperatures. After being subjected to sterilizing temperatures for a predetermined period of time, the fuse means melts and permits the valve to close before the container is to be moved from its sterilizing environment. Thus, the container can then be stored for an extended period of time with assurance that the sterility of its contents will be maintained until they are ready to be used.

In a preferred arrangement, the valve may be manually opened to relieve the vacuum within the container, thus permitting removal of the container lid for access to the contents. Once the valve is opened, the fuse means, which is rigid at normal temperatures, holds the valve in its open position, thus, the valve is cocked and ready for resterilization without any further attention. This factor is very important in that it eliminates possible human error of failing to open a valve when the container is to be reused in a sterilizing operation.

An another feature of the invention, a sealing gasket between the lid and base of the container acts as a one-way valve which will not permit flow into the container but will permit flow out of the container with a sufficient pressure differential. Thus, during the vacuum phase provided by most autoclaves at the completion of the high pressure steam phase, some of the steam within the then sealed container may be withdrawn past the gasket. This also applies a limited vacuum to the interior of the container, which is desirable during storage. The presence of the vacuum actuates an indicator which tells that the vacuum exists and thus that the contents should still be sterile. When the valve is open to relieve the vacuum, a noise is also usually heard which would indicate the vacuum and tell the user that the contents should still be sterile.

In another form of the invention disclosed, the valve provided is disposable. A rubber-like valve member snaps into a wall of the container to close one or more openings leading into the container. Before insertion of the valve member, it is provided with a fuse element which holds the valve in a configuration wherein it does not close the openings leading into the container. This fuse element melts at a desired point at the end of the sterilization phase, allowing the valve member to snap to its normally closed position, closing the openings in the container. When the container is to be opened, the valve member can be simply pulled away from the container and discarded. A new valve is then installed when the container is to be reused.

For a more thorough understanding of the invention, refer to the following detailed description and drawings in which:

FIG. 4 is a plan view of the container valve;

FIG. 5 is a cross-sectional view of the valve of FIG. 4 showing the valve in closed position;

FIG. 6 is a cross-sectional view of the valve showing the valve in open position;

FIG. 7 is a perspective view of a member used in holding the valve open;

Figure 1:
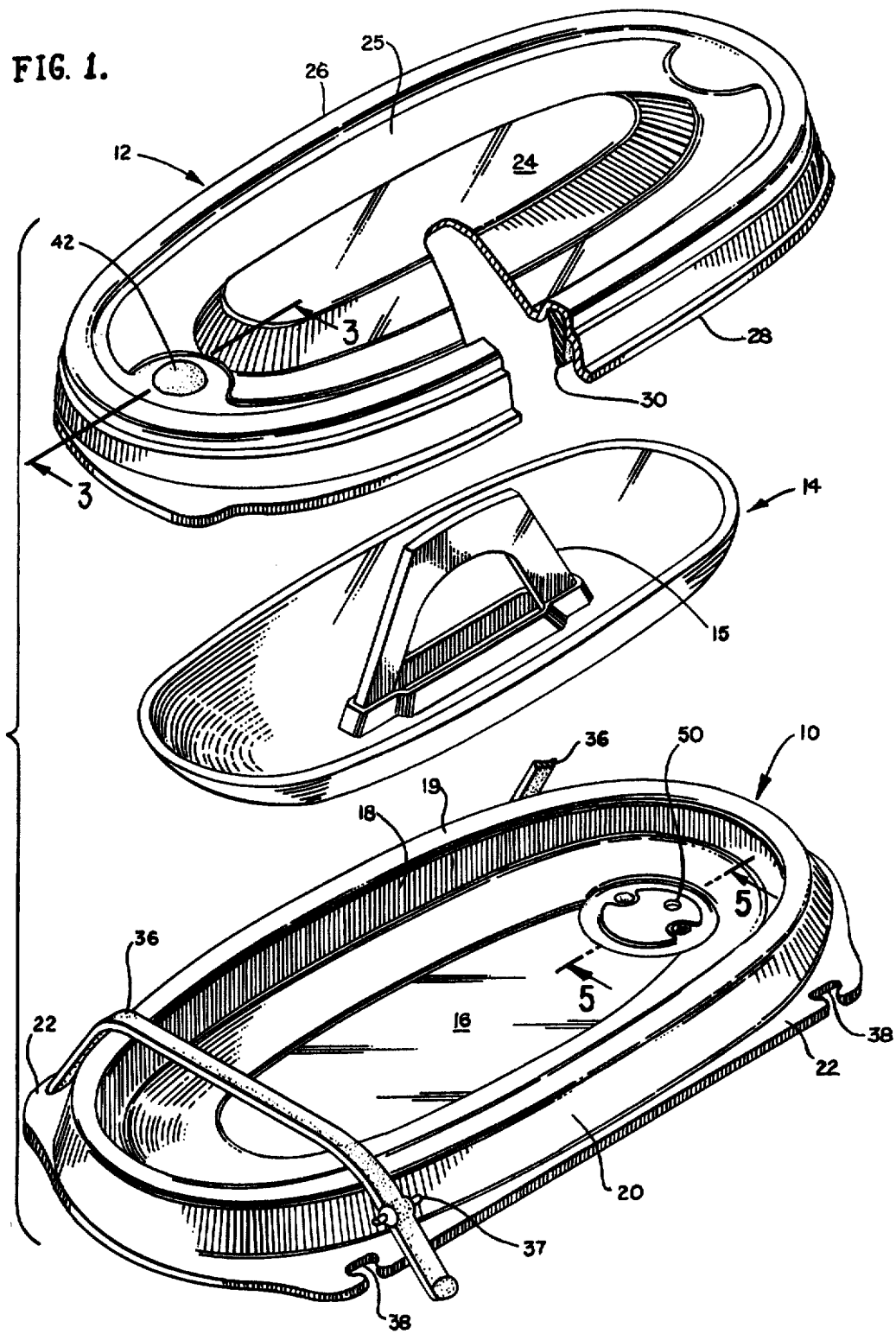
FIG. 1 is an exploded perspective view of the container of the invention showing the lid, and internal tray and the base.

Referring now to the drawings, the container shown in FIG. 1 includes a base 10, a cover or lid 12 and an internal support or tray 14. As can be seen, the container is elongated and relatively flat having rounded corners so as to provide a somewhat racetrack configuration. The base has a bottom wall 16 and a side wall 18 which terminates with a rounded upper edge 19 and a downwardly sloping flange 20, and a further horizontally extending flange portion 22. The lid 12 has a top wall with a central flat section 24 and a rounded, downwardly sloping section 25, and a surrounding edge portion 26 which slopes upwardly, horizontally, and then downwardly and outwardly to form a shape which fits over the upper edge 9 of the base 10. The lid further includes a short outwardly extending peripheral flange 28.

Figure 2:
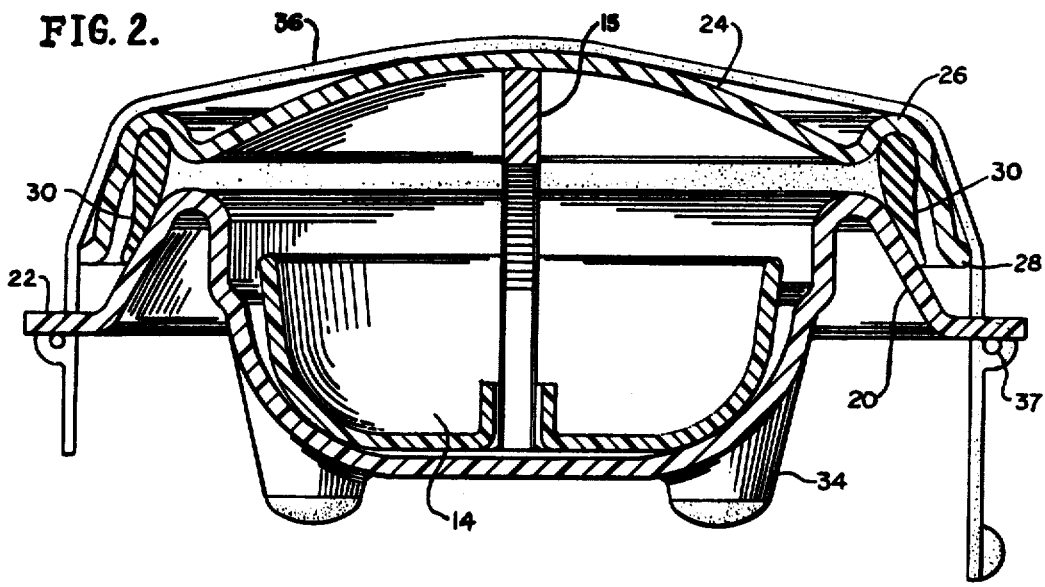
FIG. 2 is a cross-sectional view of the container.
Figure 3:
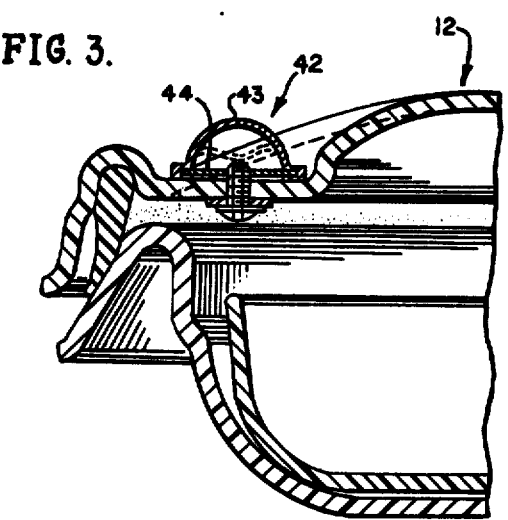
FIG. 3 is a cross-sectional view on line 3—3 of FIG. 1, illustrating a vacuum indicator.

A large flexible gasket 30, shown more clearly in FIG. 2 is attached to the lid 26 and includes a downwardly extending flexible portion which resiliently engages the downwardly and outwardly flaring wall 20 of the base. With the lid pressed tightly onto the base, a seal is formed where the lower edge of the gasket 30 engages the wall 20 as illustrated in FIG. 2. Also, the upper end of the gasket fits snuggly within the lid to form a seal in that area. As also seen from FIG. 2, the base has a plurality of legs 34 supporting the bottom wall of the base slightly from the supporting surface.

The container is further provided with a pair of flexible retaining straps 36, one on each end of the container. The strap 36 has a retaining pin 37 on each end to fit within a slot 38 formed in the flange 22, and holds the end of the strap in that position. The strap extends over the lid to positively hold it into position, and to maintain the container sealed after it is sterilized.

The tray 14 has a configuration which conforms to the interior of the base 10, and has an upwardly extending handle 40 dimensioned and shaped to engage the inner surface of the lid 12 when the lid is tightly sealed on the base. The handle provides additional support to the cover in the event a strong vacuum exists within the container.

A vacuum indicating unit 42 is mounted in one end of the cover 12. The unit 42 includes an upper resilient member 43 which is held in sealed position against the cover by a plate 44 which fits within a recess in the flexible member 43. The plate is urged in a direction towards the cover by means of a screw threaded through the cover from its lower side. The screw 46 has an internal passage therethrough so that the interior of the valve member 43 is exposed to the pressure within the container.

As shown in FIG. 1, one or more valve openings 50 are formed in the lower wall 16 of the base 10. Referring now to FIG. 5, it may be seen that the lower wall of the container is formed with an annular outwardly extending protuberance 52 having an outwardly facing surface 53. The wall then extends inwardly slightly, thus creating a shallow, circular recess or cavity 54 and a circular wall section 55.

A valve assembly 58 is attached to the circular wall section 55 by suitable fastening means. The valve assembly 58 includes a valve member 60 made of rubber-like material and having a flat circular bottom 62 and an upwardly extending annular side wall 64 having an inner surface which resiliently engages the outwardly extending wall surface 53 to seal access from the container exterior into the interior by way of the valve opening 50. A pair of stiffner plates 65 and 66 are embedded in the bottom wall 62 of the valve member 60 to provide some rigidity to the bottom wall. A pair of mounting screws or pins 68 are attached to the plate 65, and extend through support tubes 70, through holes in the wall 55 and are secured to the wall 55 by suitable nuts 72 threaded onto the end of the screws 68. The nature of the connection is such that the annular wall 64 of the valve member 60 is biased into sealing engagement with the wall surface 53 in a normally closed position.

One edge of the valve member 60 is formed with an upperwardly and outwardly extending portion which forms a manually operable valve opening lever 74. An extension of the plate 66 is embedded in the lever portion 74 so that when the lever 74 is manually depressed, the valve member may be moved into an open position as shown in FIG. 6. As stated, the resiliency of the valve member 60 is such that it normally wants to assume the position shown in FIG. 5. If desired, suitable spring means may also be employed to further urge the valve member into closed position. As one arrangement, a coil spring 75, FIG. 4, may be positioned in the uppersurface of the wall 60 of the valve member with one end of the coil engaging the plate 65 and the other end engaging the plate 66 in a manner to provide a force which biases the valve member into its closed position.

To hold the valve in the open position, there is provided a holding or cocking means which includes a support member 76 suitably attached to the plate 66 and the bottom wall 62 of the valve member 60. The support member has a pair of upwardly extending arms 77 as shown in FIG. 4. A latching lever 78 is pivotally mounted to a pin 80 supported by the arms 77 of the support 76. Urging the latching lever 78 into a clockwise direction as viewed in FIGS. 5 and 6 is a suitable spring 81 positioned on the pin 80.

A small housing 82 is attached to the other half of the valve member 60 and the plate 65 by means of the mounting screws 68. The support housing includes a shallow compartment 83 filled with a metal fuse 84 which will melt at a desired temperature. The metal is sealed within the housing by a cover plate 85 also held in place by the mounting screws 68. An irregular shaped latch 86 is pivotally mounted on the housing 82 with one end of the latch 86 being journaled adjacent the metal fuse 84, and a tang 87 on the latch 86 is positioned within the fuse metal 84. A spring 91 has one end attached to the latch 86, while the opposite end of the spring is anchored beneath one of the support posts 70. The spring 91 urges the latch 86 into a counter clockwise direction as viewed in FIG. 5.

Rigidly attached to the latch 86 is a small somewhat U-shaped portion 88 having a latching leg 89 and a shorter cam leg 90 both of which cooperate with the end of the latch lever 78 in holding the valve member in the open position and releasing it from the open position.

Turning now to the operation of the embodiment of FIGS. 1–7, assume the container is empty and that the cover or lid 12 is separate from the base 10. The items to be stored are placed within the container and the cover is placed into position on the base. The cover is held in this position by extending the straps 36 over the top of the cover and hooking the ends of the straps into the notches 38 formed in the base. Assume that the valve member 60 is in the open position of FIG. 6 and that the fuse metal 84 is solid. In this condition, the valve member 60 is held open position by virtue of the fact that the end of the latch lever 78 engages the side of the latch leg 89 as shown in FIG. 6.

The container is then placed within an autoclave or other sterilizing apparatus. If an autoclave is used, one or two vacuum phases are applied to the interior of the autoclave to draw contaminated air from the container. Since the valve is open, the air within the container is drawn out of the hole 50 in the bottom wall section 55. When steam or other sterilizing fluid is applied to the exterior of the container, it can flow freely into the interior of the container through the opening 50. The high temperatures associated with the sterilizing operation will melt the fuse metal 84 after a predetermined time which is selected to be some time after the container and its contents have been sterilized. Preferably, this would be towards the end of the heating cycle and before the final vacuum cycle as typically applied in an autoclave to remove the steam from the autoclave. When the fuse metal 84 melts, the resiliency of the valve member 60 plus the urging of the spring 75 will move against the latching leg 89 pivoting the member 86 against the urging of the weaker spring 91. The tang 81 is permitted to move within the fuse metal since the metal is no longer rigid. As the U-shaped member 88 pivots with the member 86, the cam leg 90 engages the upper surface of the latch lever 78 camming it downwardly against the biasing of the spring 81 until the tip of the lever 78 slips past the lowrer edge of the leg 89. Once this occurs, the valve member quickly moves to the position shown in FIG. 5 wherein the flexible wall 64 of the valve member is once more sealed against the wall surface 53. The latch lever 78 is depressed beneath the end of the latch leg 89. Note that the spring 91 urges the member 86 into the position shown wherein the end of the lever 78 is engaged on the end of the leg 89. Note also that the end of the leg 89 is beveled at the approximate angle of the orientation of the lever 78 in the valve closed position.

The container is now sealed with its contents sterilized so that the container can be removed from the sterilized atmosphere. However, as indicated above, if the unit is sterilized within an autoclave, there will usually be a further vacuum phase after the valve is closed. If the autoclave pressure surrounding the container becomes significantly less than the pressure within the container, the atmosphere within the container can leak from the container, past the flexible gasket 30. This is due to the configuration of the flange surface 20 on the base 10 and due to the size and flexibility of the lower end of the gasket. Since the relationship between the flexible wall 64 and the surface 53 is somewhat similar, it is possible that some pressure relief may occur at that area too. This leakage is desirable in that there may be some residual steam within the container and it is preferable that the container be relatively dry.

With a strong vacuum applied to the exterior of the container, a vacuum will be created on the interior. Thus, once the pressure is brought back to atmospheric, a vacuum will exist within the container; and neither the gasket nor the valve will permit leakage into the container. The curved configuration of the container is such that its walls can withstand a relatively high pressure differential between the interior and exterior of the container. However, as a precautionary measure with larger size containers, it may be desirable to have the handle 40 of the tray 14 engage the interior upper surface of the lid as shown in FIG. 2 to provide additional strength.

The container with its contents may now be moved to whereever desired such as to storage for future use or it may be carried directly to where its contents are to be used. When the container is to be opened, it is first necessary to relieve any vacuum that may exist. To do this, it is only necessary to depress the valve lever 74 moving the valve into the open position. The sound accompanying the vacuum relief will indicate that the contents of the container are still sterilized. Conversley, if leakage has occured, the absence of the sound will warn the individual opening the container that the contents may no longer be sterile. The flexible member 43 of the indicator 42 will also tell the condition, by being depressed when there is vacuum and raised when there is no vacuum.

Due to the excellent nature of the seal provided by the gasket 30, it is quite likely that even though air molecules may, after a long period of time, seep into the container past the gasket, most microorganisms are much larger and cannot necessarily pass the seal. Thus, to that extent, the gasket serves as a filter even if the vacuum is ultimately lost.

Shortly after the sterilizing temperatures begin to fall, the fuse metal will once more solidify, holding the latch leg 89 in the position shown in FIG. 6. Thus, when the valve is open, the tip of the latch lever 78 will slide off the end of the latch leg 89 and be urged slightly in a clockwise direction by its coil spring 81 into engagement with the return leg 90. When the lever 74 is released, the end of the latch lever 78 once more engages the side of the latch leg 89 holding the valve in its open position. Thus, depressing the lever 74 not only relieves the vacuum within the container but simultaneously cocks the valve member in an open position so that the container is once more ready to be sterilized. This feature is very important in that it is not necessary for a person to remember to open the valve before placing the container back into the sterilizing apparatus. Thus, if the container has been used to sterilize surgical instruments for example, and the container is taken directly into the operating room, the instruments can be removed directly from the container, used, washed if necessary, and then returned to the container for resterilization.

If it is preferred that the container not be taken directly into the operating room, the container may be opened just outside the operating room and only the sterile tray and the instruments on the tray be carried into the operating room. Again, after the instruments are used, they can be returned to the tray and the tray returned to the container for resterilization. It is only necessary that the cover be once more strapped into position and the container can then be placed within the autoclave for sterilizing.

As a further variation of this procedure, the container may be placed within a sterilizing bag (not shown) during the sterilizing cycle. This is a bag available on the market, sold by C. K. Bord Inc. and described in U.S. Pat. No. 3,595,465 into which the container could be placed and inserted into the autoclave. The bag is such that is will permit steam to penetrate it during the sterilizing cycle but will be sealed to a considerable extent during the sterilizing cycle. With this situation, the container would be removed from the bag just prior to be taken into the operating room. Thus, the entire container would still be reasonably sterile and the instruments could be taken directly from the base of the container. The upper edge of the base would still be sterile in the event a person's hand should touch that area in removing instruments.

Figure 8:
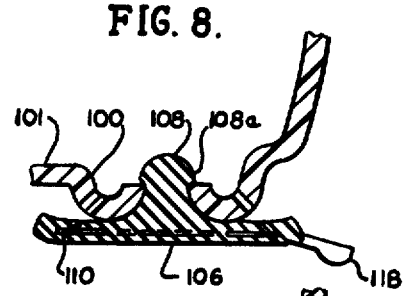
FIG. 8 is a cross-sectional view of a second embodiment of a valve member for the container of FIG. 1, the valve being shown in open position.
Figure 10:
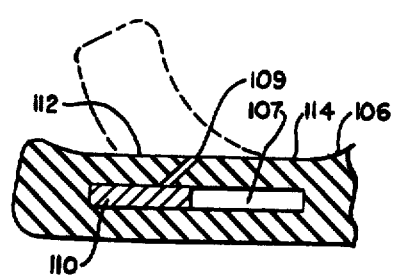
FIG. 10 is an enlarged fragmentary view showing a portion of the valve of FIG. 8 in the open position with solid lines, and in closed position in dotted lines.
Figure 9:
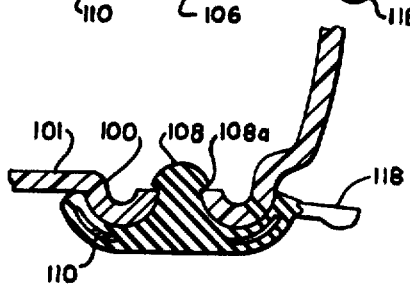
FIG. 9 is a cross-sectional view of the valve of FIG. 8 with the valve in closed position.

One of the advantages of the arrangement described above is that the valve as well as the container is reuseable. However, as another approach, there is illustrated in FIGS. 8-10 a second embodiment of the invention comprising a disposable, simplified valve still using the fuse principle. As seen in FIG. 8, a small annular protuberance 100 is formed in the wall 101 of a container similar to that shown in FIG. 1. One or more holes 102 are formed in the annular wall 100 to permit access to the container. An additional hole is formed in the middle of the annular wall 100 to receive a disposable valve member 106 provided to control access to the container through the holes 102. More specifically, the valve member 106 includes an integral, inwardly extending projection 108 which is rounded and sized so that it can be pushed into the hole in the center of the annular wall 100 as shown in FIG. 8. A peripheral shoulder 108a engages the interior wall of the container to hold the valve in position on the container.

The valve member 106 is formed of a resilient rubber-like material which permits the projection 108 to be forced into the hole in the container wall. The member 106 is molded in the configuration shown in FIG. 9 which comprises a circular shape with the periphery of the member curving upwardly into a saucer configuration tightly engaging the outer surface of the annular wall 100 and enclosing the valve openings 102 into the container. Thus, in the condition shown in FIG. 9, the valve is closed which might be though of as its normal condition in that that is the position the rubber valve member 106 wants to assume. Note also that if a vacuum exists within the container, the vacuum helps hold the valve member tightly against the holes 102.

To hold the valve in its open position, there is provided a fuse 110 in the form of a ring having a flat, washer shaped configuration. As seen in FIG. 10, the valve member 106 is formed with an internal slot 107 with a smaller diagonal slit 109 forming two resilient flaps 112 and 114. After the valve member is molded into the configuration shown in FIG. 9, the fuse element is inserted into the slot within the valve member by depressing the periphery of the valve member so that the fuse washer may be inserted into the slot 107 through the slit 109. Note that the fuse occupies only the outer portion of the slot 107. With the fuse so positioned, the configuration of the valve member is as shown in FIG. 8 wherein the outer periphery of the outer valve member is held away from the openings 102. The valves would normally be furnished in this condition. Thus, a user of the container can simply take a valve of this type and snap it into the container in the position shown in FIG. 8. The container is then ready to be sterilized.

At the appropriate time in a heat sterilizing cycle, the fuse washer will melt, allowing the valve member to assume its normal molded position, as indicated by the broken lines in FIG. 10. Thus, the valve is closed as shown in FIG. 9. The closing movement of the valve member together with gravity causes the melted fuse metal to flow to the inner end of the slot 107 within the valve member as shown in FIG. 9. Thus, when the fuse metal once more solidifies, it will not interfere with the sealing operation of the valve. Instead, it will tend to hold the valve in the closed position to some extent.

When it is desirable to release the vacuum within the container, an integral tab 118 formed on one edge of the valve member is pulled away from the container thus allowing the vacuum to be relieved through the adjacent hole 102. The container lid can then be removed. The valve member 106 can also be removed by simply pulling harder on the valve tab. When the container is to be resterilized, a new valve member can be quickly snapped into position. A new valve member can, of course, be installed as soon as the old one is removed.

What is claimed is:
1. Apparatus for holding items being sterilized and for storing such items after sterilization, comprising:
means forming a closed container including a base, a lid and a flexible gasket having means for sealing the lid to the base in a manner which permits gaseous leakage past the gasket means out of the container when a vacuum is applied to the container exterior but prevents air flow into the container when said vacuum is removed; and
valve means including an opening in one of the container walls, a valve member for controlling fluid flow through the opening, means urging the valve member closed, and means for holding the valve member in an open position so that sterilizing gases applied to the container exterior can enter the container, said holding means including temperature responsive means which is in one condition at normal room temperatures and is arranged to hold the valve member open but changes to a second condition at sterilizing temperatures after the container and its contents are sterilized, to permit the valve member to close.

2. The apparatus of claim 1 wherein said valve member is manually openable to release any vacuum which may have formed in the container, and said temperature responsive means, when in said one condition, will hold the valve member open when the valve member is opened manually to relieve the vacuum.

3. The apparatus of claim 2 wherein said valve member comprises a resilient, flexible member which normally assumes a position closing the valve opening, and said means for holding the valve member in open position includes a lever attached to said valve member which cooperates with said temperature responsive means to hold the valve member in open position when the temperature responsive means is in said one condition, and to release the lever from holding position when the temperature responsive means is in said second condition.

4. The apparatus of claim 3 wherein said temperature responsive means comprises a sealed quantity of material which is solid at normal room temperatures and becomes liquid at sterilizing temperatures, and a member extending into said material so that relative movement between the capsule and said member is prevented when said material is rigid but is permitted when the material is not rigid so that said lever can move.

5. The apparatus of claim 4 wherein said container wall has an annular protuberance surrounding said opening and said valve member is a resilient, flexible member including a side wall which engages said protuberance to control flow through said opening, and including means for mounting said valve member and said holding means to said container wall.

6. The apparatus of claim 1 wherein said valve member comprises a resilient flexible member which snaps into the container and which is self-biased into a position closing said opening.

7. The apparatus of claim 1 wherein said valve member comprises a resilient flexible member having a saucer-like configuration with its inner surface shaped to conform to said container and close said openings, and said temperature responsive means fits onto said valve member to hold the member in a flatter configuration wherein the inner surface of the valve member is spaced from said opening.

8. The apparatus of claim 7 wherein said temperature responsive means has a flat washer-like shape which snaps into a slot on the inner side of said valve member to hold said valve member in its open position.

9. The apparatus of claim 8 wherein said slot in said valve member includes space for receiving the melted temperature responsive material in a location which will not interfere with manual opening of the valve member.

10. Apparatus for containing items as they are being sterilized and for storing such items after sterilization, comprising a base, a lid cooperating with the base to form a closed container, said base and lid having mating peripheral portions including a downwardly and outwardly sloping flange formed on one of said lid and base, a flexible gasket sealing the lid to the base including a free flexible end having one side engaging said flange and the other side of said flange end exposed to gaseous pressure on the exterior of the container in a manner which permits said end to move away from the flange and thus permit gaseous leakage past the gasket out of the container when a vacuum is applied to the exterior of the container so that a vacuum is also created within the container, but said free end being sufficiently resilient to return to a position engaging said flange when said vacuum is removed to prevent leakage past the gasket into the container so that when the exterior of the sterilized container is exposed to unsterile air it cannot enter the container, a valve in one of the container walls for permitting sterilizing fluid to flow into the container, and means for automatically closing the valve when the container and its contents have been sterilized.

11. The apparatus of claim 10 wherein said closing means is responsive to the temperature of said sterilizing fluid.

12. The apparatus of claim 10 wherein said valve closing means includes temperature responsive means for closing the valve after the container contents are subjected to sterilizing temperatures for sufficient time to sterilize the container and its contents.

13. The apparatus of claim 10 wherein said base has side walls terminating in a rounded upper edge and said flange slopes downwardly and outwardly from the upper edge, said lid having a similarly shaped flange to fit over said base flange, and said gasket is carried by the lid flange and engages the downwardly sloping surface of said base flange to seal the container.

14. The apparatus of claim 10 wherein said valve includes a valve opening in a wall of said container, means defining an annular wall surrounding the valve opening and tapering from the container wall to a smaller diameter, a valve member having flexible side walls which mate with said annular wall surrounding the valve opening so as to prevent fluid flow into the container through the valve opening while permitting fluid flow out of the valve opening if a sufficient pressure differential exists across the valve member.

15. The apparatus of claim 14 with said valve closing means including temperature responsive means for holding said flexible valve member in an open position wherein steam or other sterilizing fluid applied to the container exterior may enter the container, said temperature responsive means being adapted to no longer hold the valve member in an open position after being subjected to sterilizing temperatures for a predetermined period of time.

16. A valve member for controlling fluid flow through a valve opening, said member including means made of flexible resilient material having a saucer-like configuration with its inner surface shaped to conform to the structure surrounding the valve opening and thus sealing the opening, and temperature responsive means captured within said flexible means to hold said flexible means in a configuration wherein it does not conform to said structure so that the valve opening is not closed, said temperature responsive means including means for changing its condition at a predetermined temperature to permit said flexible means to close the valve opening.

17. The valve member of claim 16 wherein said changing temperature responsive means includes means which when below said predetermined temperature is arranged to hold said flexible means in a flatter configuration.

18. The valve of claim 17 wherein said temperature responsive means is washer shaped and fits within a slot formed in said flexible means.

19. A valve member for controlling fluid flow through a valve opening, said member including means made of flexible resilient material molded to conform to structure surrounding the valve opening to seal the opening, said member being self biasing into sealing position when mounted on said structure, temperature responsive means to hold said flexible means in a configuration wherein it does not seal said opening, said temperature responsive means changing its condition at a predetermined temperature to permit said flexible means to seal the valve opening, and said member including a resilient projection for insertion into a hole in said structure for mounting said member on the structure, said projection having shoulder means which can be forced through said hole and will engage the structure surrounding the hole to retain the valve member in position.

20. The valve member of claim 19 wherein said member is constructed to permit gaseous flow out of the container in the sealed position upon application of sufficient pressure differential across said member.

21. A method of sterilizing comprising the steps of:
placing items to be sterilized into the base of a container which is strong enough to withstand normal atmospheric pressure on its exterior when its interior has a high vacuum environment;
placing a lid on the base with a gasket therebetween which when engaging the lid and the base prevents flow into the container but permits flow out of the container;
placing the container in a sterilizer with the exterior of the container in fluid communication with the interior;
operating the sterilizer to provide a sterilizing cycle including replacing the air in the container with a sterilizing environment to sterilize the items, and then applying a vacuum to the container exterior to withdraw the sterilizing environment in the container; and automatically sealing said container by means responsive to the environment in the sterilizer before unsterile air is admitted to the sterilizer at the end of said cycle so that the sterilized items remain sealed in the container in a substantially atomosphere-free environment when the container is removed from the sterilizer.

22. The method of claim 21 wherein said sealing step includes closing the container to prevent gaseous flow into the container while permitting flow out of the container when the pressure in the container exceeds the exterior pressure, said seal improving when the pressure on the exterior increases relative to the interior pressure, and the initial closing of said container to prevent inflow occurs after said items are sterilized but before the sterilizing environment is withdrawn from the container.

23. The method of claim 22 wherein said closing is temperature responsive and occurs near the end of the sterilizing environment of said cycle.

24. The method of claim 21 wherein said container includes a valve in a wall of the container, and wherein said lid is placed on the base with the gasket engaging the lid and base sufficiently to prevent flow into the container and with said valve open, when the container is placed in the sterilizer, and said valve is automatically closed near the end of said sterilizing cycle by said means responsive to the environment, and said lid is drawn more tightly onto said base by the vacuum applied to the container exterior.

* * * * *